United States Patent [19]

Nash

[11] Patent Number: 4,571,183

[45] Date of Patent: * Feb. 18, 1986

[54] VIBRATORY ENDODONTIC DEVICE

[75] Inventor: John E. Nash, Downington, Pa.

[73] Assignee: Syntex (U.S.A.) Inc., Palo Alto, Calif.

[*] Notice: The portion of the term of this patent subsequent to Nov. 27, 2001 has been disclaimed.

[21] Appl. No.: 523,833

[22] Filed: Aug. 18, 1983

Related U.S. Application Data

[63] Continuation-in-part of Ser. No. 433,075, Oct. 6, 1982, Pat. No. 4,484,891.

[51] Int. Cl.⁴ .............................................. A61C 1/16
[52] U.S. Cl. .................................... 433/116; 433/127; 433/118
[58] Field of Search ............... 433/116, 118, 119, 120, 433/122, 123, 124, 147, 75, 126, 127

[56] References Cited

U.S. PATENT DOCUMENTS

| Re. 29,687 | 7/1978 | Sertich | 433/120 |
|---|---|---|---|
| 349,338 | 9/1886 | Buschemeyer | 433/122 |
| 1,046,560 | 12/1912 | Coylson | 433/122 |
| 1,821,079 | 9/1931 | Schultze | 433/122 |
| 2,485,900 | 10/1949 | McKeen | 433/116 |
| 2,690,617 | 10/1954 | Giern et al. | 433/147 |
| 3,037,282 | 6/1962 | Aktarian et al. | 433/128 |
| 3,058,218 | 10/1962 | Kleesattel et al. | 433/119 |
| 3,124,878 | 3/1964 | Bodine et al. | 433/119 |
| 3,518,766 | 7/1970 | Burt | 433/119 |
| 3,578,745 | 5/1971 | Garnier | 32/57 |
| 3,763,411 | 10/1973 | Goof | 433/119 |
| 3,786,566 | 1/1974 | Jelicic et al. | 433/116 |
| 3,892,040 | 7/1975 | Marquis | 433/147 |
| 3,961,422 | 6/1976 | Riitano et al. | 32/57 |
| 3,962,790 | 6/1976 | Riitano et al. | 433/81 |
| 4,019,254 | 4/1977 | Malmin | 32/57 |
| 4,028,810 | 6/1977 | Vice | 32/57 |
| 4,165,562 | 8/1979 | Sarfatti | 32/57 |
| 4,182,040 | 1/1950 | Bechtold, Jr. | 433/77 |
| 4,217,098 | 8/1980 | Garnier | 433/147 |
| 4,229,168 | 10/1980 | Scholz | 433/124 |
| 4,262,252 | 5/1981 | Lustig | 433/116 |
| 4,295,827 | 10/1981 | Martin et al. | 433/119 |
| 4,330,278 | 5/1982 | Martin | 433/81 |
| 4,484,891 | 11/1984 | Nash | 433/116 |

FOREIGN PATENT DOCUMENTS

| 0015672 | 9/1980 | European Pat. Off. | |
| 808873 | 7/1949 | Fed. Rep. of Germany | 433/118 |
| 1084870 | 7/1960 | Fed. Rep. of Germany | 433/75 |
| 3010636 | 10/1981 | Fed. Rep. of Germany | 433/119 |
| 3105424 | 1/1982 | Fed. Rep. of Germany | |
| 1325071 | of 1963 | France | |
| 602086 | 7/1978 | Switzerland | 433/116 |
| 0830142 | 3/1960 | United Kingdom | |

Primary Examiner—John J. Wilson
Attorney, Agent, or Firm—Derek P. Freyberg; David A. Lowin; John A. Dhuey

[57] ABSTRACT

A vibratory endodontic device is described for mechanical preparation of dental radicular canals, i.e., root canals, prior to their obturation. The device includes a housing, a vibratory drive means supported within the housing to minimize the transfer of vibration to the housing, an endodontic file connected to the drive means for vibratory movement and stop means operatively connected to the housing and substantially isolated from the mechanical vibrations created by the vibratory drive means. Additionally, fluid transport means are provided for maintaining a controllable or a continuous flow of irrigation fluid along the endodontic file. Various assemblies for retaining the endodontic files and the stop means at the operative end of the vibrating device are also described.

25 Claims, 22 Drawing Figures

VIBRATORY ENDODONTIC DEVICE

CROSS-REFERENCE TO RELATED APPLICATION

This application is a continuation-in-part of my copending application Ser. No. 06/433,075, filed Oct. 6, 1982, now U.S. Pat. No. 4,484,891.

BACKGROUND OF THE INVENTION

1. Field

This invention relates generally to mechanically driven endodontic instruments. In particular, it relates to a vibratory endodontic device having stop means that are substantially isolated from the mechanical vibrations created by the vibratory drive mechanism of the device, to limit travel of the endodontic file during use and, optionally, having fluid transport means for transporting irrigation fluid to the endodontic file.

2. State of the Art

Mechanically driven endodontic instruments have been described previously, as for example in U.S. Pat. Nos. 3,578,745 to Garnier and 3,962,790 to Riitano et al. Vibratory endodontic instruments have also been proposed, for example in U.S. Pat. No. 4,019,254 to Malmin, where it is stated that "Applicant is unaware of any ultrasonically activated root canal instruments" and goes on to describe a diamond grit-coated endodontic instrument for use with any source of energy, including ultrasonic activation. In U.S. Pat. No. 4,295,827 to Martin et al., an endodontic flow through ultrasonic instrument holder attachment is described to fit any ultrasonic transducer mechanism and mount a endodontic drill file at its end, the holder including a fluid transport tube surrounding the file below its point contact means. The motion at the tip of the file is described as circular-like and/or ellipsoidal or oval, with criss crossing motions at other parts of the file. Martin does not, however describe the instrument holder attachment in any detail, simply calling for a connecting means suitably sized to fit into the ultrasonic transducer mechanism and be affixed to the water transport. Martin gives no description of a sonic vibratory endodontic instrument or the attachment means and mechanisms required to make one. There remained a need for a sonic vibratory endodontic device with both circular-like and up-and-down motions generated by the energizing means.

Various stops have been described for limiting the depth of insertion of endodontic files during use. See for example, U.S. Pat. Nos. 3,961,422 to Riitano et al.; 4,028,810 to Vice; 4,165,562 to Sarfatti and 4,182,040 to Bechtold, Jr. Conventional methods of controlling the depth of insertion of mechanically driven endodontic files have not been satisfactory. When conventional stops are placed directly on the endodontic files which are driven by mechanical devices, the stops tend to fail rapidly themselves and also tend to increase the failure rate of files used therewith. Additionally, the added mass to the stop on the file tends to affect the vibratory action of the file and the control thereof.

Accordingly, there is a need for an improved stop mechanism, particularly for use with mechanically or electrically driven vibratory endodontic files.

It is an object of the invention to provide a sonic vibratory endodontic device.

Another object of the invention is to provide a sonic vibratory endodontic device wherein an endodontic tool is vibrated both circularly and up-and-down at its working end.

Still another object of the invention is to provide a sonic vibratory endodontic device which satisfies the foregoing objects and can be added as an attachment to an existing source of sonic vibrations.

Another object of the invention is to provide an endodontic device that is easier to use than the previous devices.

A further object of the invention is to provide an endodontic device that requires a smaller inventory of files than did the previous devices.

A still further object of the invention is to provide an endodontic device reduces fatigue for the endodontist while performing endodontic procedures.

Another object of the invention is to provide an endodontic device that follows curved canals faithfully, continues to work in tight canals where horizontal vibratory motion is precluded, and which has a greatly reduced incidence of file breakage.

Yet another object of the invention is to provide a stop mechanism for use with a mechanically or electrically driven vibratory endodontic file.

A still further object of the invention is to provide a stop mechanism that is easy to attach and set, Another object of the invention is to provide a stop mechanism for a vibratory endodontic file, which stop mechanism is substantially isolated from the vibrations of that file.

Other objects and advantages of the present invention will become apparent to those skilled in the art from the following summary, description and the drawing.

SUMMARY OF THE INVENTION

As used herein, the term "mechanically driven" or "mechanical" includes vibratory devices and those devices which are powered by means other than the dentist's or doctor's hand. Such mechanically driven vibratory devices are intended to include strictly mechanically driven devices such as gear driven handpieces which impart an oscillatory, to-and-fro motion to a work tool, fluid driven devices such as those of the type more particularly described herein and electrically driven devices.

The present invention in one aspect is a vibratory endodontic device comprising a housing; vibratory drive means within the housing; means supporting the vibratory drive means within the housing, the supporting means substantially preventing transfer of vibration between the vibratory drive means and the housing; a work tool (such as an endodontic file) operatively connected to the vibratory drive means; and stop means operatively connected to the housing for limiting travel of the work tool between selected positions during use thereof, whereby the stop means is substantially isolated from vibration created by the vibratory drive means.

In another aspect, the invention is directed to an assembly for attaching a work tool (i.e., endodontic file) to a vibratory device, such assembly comprising an elongated mandrel having a first end for attachment to the vibratory device and a second end for supporting the work tool, and retaining means on the second end of the mandrel for retaining the work tool thereon at a position where its vibratory mode will be both circular and up-and-down at the working end of the tool. A stop may also be provided for selectively limiting travel of the file when in use.

DETAILED DESCRIPTION OF THE INVENTION

Figure 1:
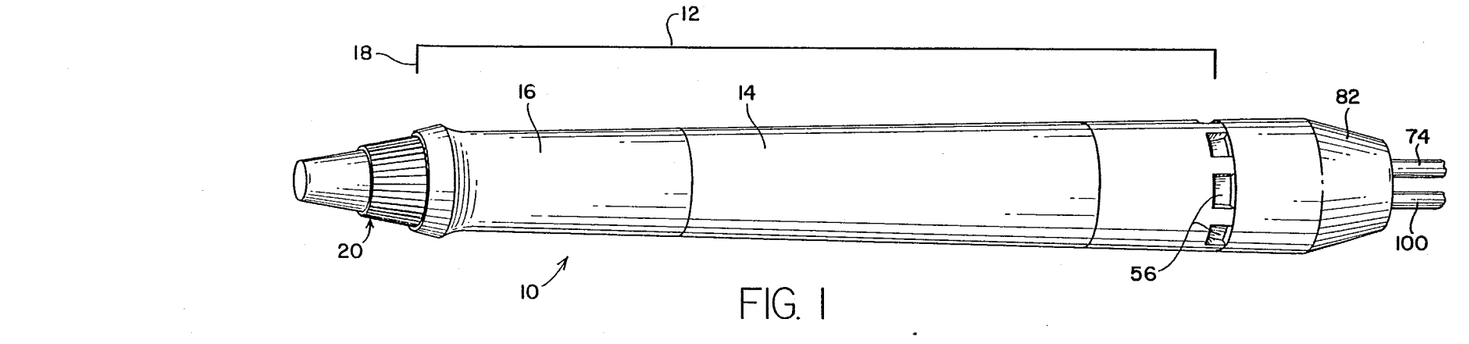
FIG. 1 is a perspective view of a representative vibratory device for powering a work tool assembly (not shown) to be attached thereto.

With reference to the drawings, the vibratory device 10 comprises a housing having a handle 12 which includes a barrel 14 and a neck 16. Attached to the distal end 18 of the vibrator 10 is a tip holder 20. Tip holder 20 is adapted to receive the shank of a work tool such as an endodontic file, as will be described more fully hereinafter. As shown in detail in the cross-sectional view of FIG. 2, handle 12 provides an elongated casing within which is mounted support means comprising a first or front support 30 including a pair of O-rings 31. A second or rear resilient support is provided by a cylindrical tube 32 of resilient material which is sleevably engaged about a boss portion 34 secured to a rigid rear support 36. Boss portion 34 has retaining grooves 38 circumferentially disposed thereon for retaining resilient rear support 32 by means of retaining ring 40. Disposed substantially coaxially with respect to elongated handle 12 is a vibratable, substantially rigid, hollow shaft 42. Tip holder 20 is threadedly connected to the distal end 44 of hollow shaft 42 via an internally threaded shaft extension 43. The proximal end of shaft 42 is formed with retaining grooves 48 for engaging resilient rear support 32 therein. A pin 73 is provided on shaft 42 for engaging a wall 75 of a slot in rear support 36 to oppose twisting forces applied to shaft 42 during engagement or disengagement of tip holder 20 with or from the distal end of shaft 42. Rear support 32 is retained within retaining grooves 48 on shaft 42 by means of a retaining ring 50.

Figure 2:
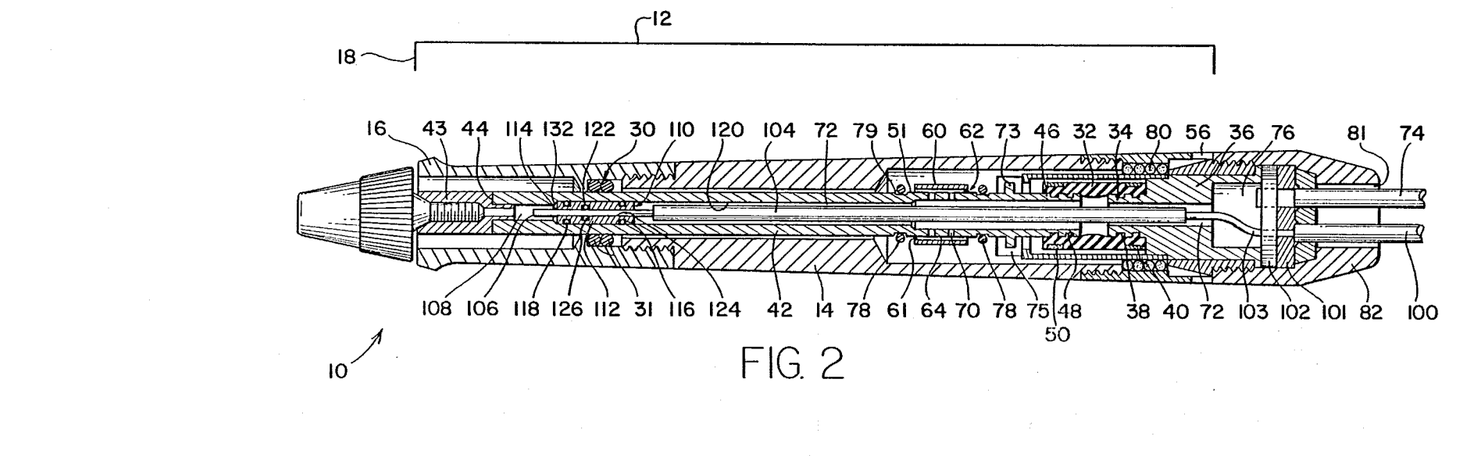
FIG. 2 is a longitudinal side elevational view, partly in section, of the vibratory device of FIG. 1.

As seen most clearly in FIG. 2, shaft 42 is formed with an intermediate section 51 having a diameter greater than the diameter of those portions of shaft 42 adjacent section 51. Outlet ports 70 are formed in the wall of shaft 42 in the intermediate section 51 and serve to provide fluid communication for fluid media means from the inside of tubular shaft 42 to the space adjacent side wall 64 of shaft 42. Centrally and axially disposed above intermediate portion 51 of shaft 42 is rotor means 60, which defines a gap 62 between its inner surface 61 and side wall 64 of shaft 42 into which fluid media is directed from outlet ports 70.

With reference to FIGS. 1 and 2, a fluid medium, such as compressed air, is supplied from a source (not shown) through a supply tube 74 which passes through an axially disposed opening 81 in end cap 82. The connection to the source may be made by a swivelable, quick connect coupling. The flow of compressed air passes into plenum 76 in through passageway 72 and shaft 42 to fluid media outlet ports 70. The flow of compressed air which exhausts through outlet ports 70 strikes the inner wall 61 of rotor 60 and urges rotor 60 to rotate about shaft 42. Each of the outlet ports 70 has an axis which is offset or spaced at a distance from the longitudinal axis of shaft 42. In that configuration no port axis intersects the longitudinal axis of shaft 42 and each of ports 70 directs a jet of air at a glancing angle with respect to the inner wall 61 of rotor 60 so as to impart rotational movement to rotor 60. The air passes through the end sections of gap 62 into the main barrel section and subsequently passes through muffler means 80 which are supported on rigid rear support 36 to exhaust through outlet ports 56.

Stop means 78 are disposed in indented sections or grooves 79 in outer surface 64 of shaft 42. Typically, stop means 78 comprise O-rings sleevably engaged about shaft 42. Stop means 78 prevent excessive travel of rotor 60 so that rotor 60 is at least partially disposed about outlet means 70 at all times, including the time prior to activation of the instrument with compressed air. Thus, when air is supplied to the instrument, the air flowing through outlet ports 70 will contact at least a portion of rotor 60 and initiate its rotational movement about shaft 42. In normal operation rotor 60 will not contact stop means 78. A more detailed description of the manner in which the spinning rotor 60 imparts vibrational movement to shaft 42 and other aspects of the vibrator may be found in the U.S. Pat. No. Re. 29,687 and No. 4,330,282, the disclosure of which ar incorporated herein by reference.

The vibrator can include means for transporting water or other fluids (e.g. medicated irrigants) from an external source to a work tool at its operative end. The fluid supply can be continuous or controllable at the option of the operator and the source does not form a part of the present invention. A first fluid transport hose 100 located at the rearward or proximal end of vibrator 10 is mounted in a detachable coupling 101. First fluid hose 100 is connected to an external source of fluid (not shown), the forward end of the hose being connected to one end of a rigid tube 103 which passes through a passageway in support body 102. Tube 103 is disposed substantially coaxially with respect to hollow shaft 42. Fluid transport tube 103 extends through hollow shaft 42 toward the distal end of scaler 10 and terminates distally from fluid seal assembly 110. Tube 103 is covered with an elastomeric tube covering 104 to dampen vibration build-up within tube 103. The forward or distal end 106 of fluid tube 103 extends into plenum 108.

Fluid tube end 106 is supportably received within a fluid seal assembly 110 located at the forward or distal end of vibrator 10. Fluid seal assembly 110 comprises a cylindrical body 112 having a passageway 114 coaxially disposed with respect to the axis of the body 112. Running circumferentially about the outer side wall of cylindrical body 112 are a pair of spaced annular grooves 116, one adjacent each end cylindrical body 112. Disposed within each of grooves 116 is an O-ring 118 fabricated of a resilient material. O-rings 118 serve to position cylindrical body 112 within the forward end of hollow shaft 42 by frictional engagement of O-rings 118 with portions of inner wall 120 of shaft 42. Within a midportion of cylindrical body 112 is a chamber formed by an annular groove 122 running circumferentially along a portion of inner wall 124 of body 112 between grooves 116. Contained within groove 122 is an O-ring 126 which is in frictional engagement with the walls of groove 122 and with a portion of fluid tube 106. O-ring 126 helps to properly position tube 104 centrally within hollow shaft 42. Positioning of the center of gravity of fluid seal assembly 110 slightly forwardly of first support 30, i.e., toward the distal end of scaler 10, imparts a force on cylindrical body 112 tending to move it in a forward axial direction toward the distal end of scaler 10, thereby ensuring continuous contact between cylindrical body 112 and shoulder 132 of shaft 42. A more detailed description of the manner in which sealing between the water assembly 110 and shaft 42 is effected is provided in U.S. Pat. No. 4,260,380, the disclosure of which is incorporated herein by reference.

Figure 3:
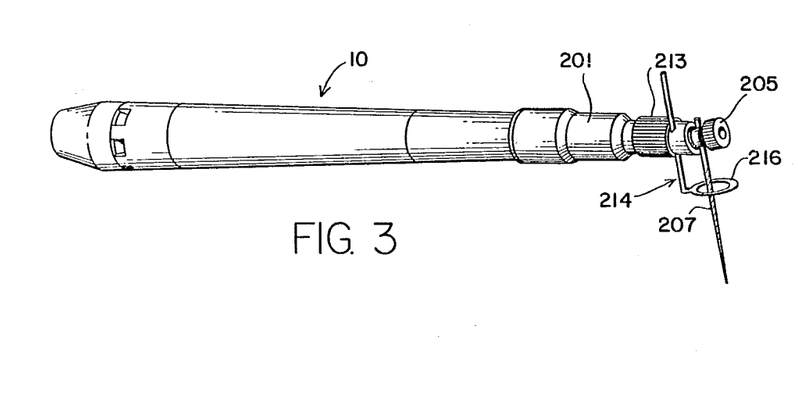
FIG. 3 is a perspective view of an embodiment of the vibratory endodontic device of the invention.
Figure 4:
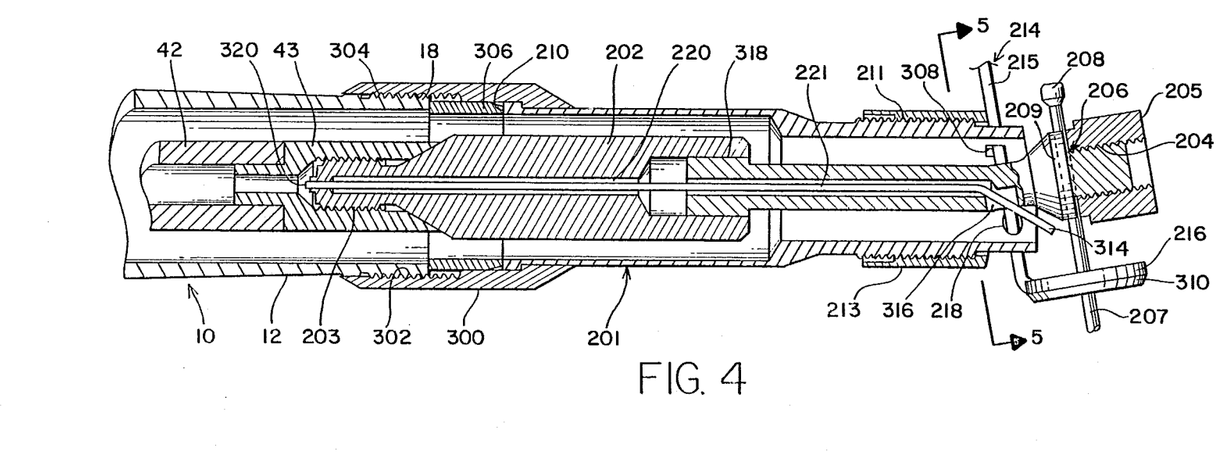
FIG. 4 is view of the work tool assembly of the device of FIG. 3 partially in section, taken along line 3—3 in FIG. 3, the vibratory device and the endodontic file being abbreviated to conserve space.
Figure 5:
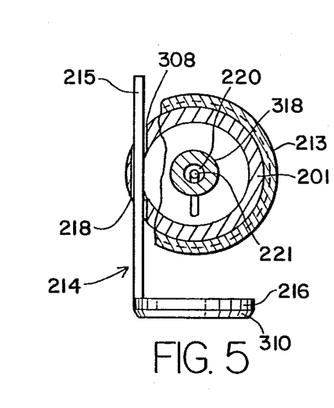
FIG. 5 is a cross-sectional view along line 5—5 of FIG. 4 illustrating the offset location of the stop means.

In a preferred embodiment of the invention, the tip holder: 20 of the vibratory device 10 is replaced by an assembly having a vibration-isolated extension 201 and a vibratable mandrel 202 for supporting an endodontic file 207. This embodiment is illustrated in FIGS. 3, 4 and 5. An end 210 of extension 201 is retained on the vibrator 10 by means of a locking ring 300 having an internally threaded portion 302 which is received on an externally threaded portion 304 of the distal end 18 of handle 12. Depending on the vibrator to which the attachment assembly is connected, a spacer element 306 can be disposed between handle 12 and extension 201 to adjust the position of the depth stop 216 with respect to the file 207. The other end of extension 201 is formed as a threaded end 211 adapted to engage a retaining ring 213 which is internally threaded. Extension 201 is formed with an upper slot 308 and a lower hole 218 to receive an adjustable stop 214 (or depth stop). Stop 214 is formed with an upper leg 215 and a depending stop surface 216 from the lower end of the leg 215. A cushioned portion 310 can be provided on stop surface 216, for example by surrounding the stop surface with a resilient material such as a rubber or plastic tube or by dipping stop surface 216 in a resilient material that will adhere to it, to cushion the impact between the depth stop and a tooth. Leg 215 is adapted to pass through openings 218 and 308 and can be moved upwardly and downwardly within those holes. When stop 214 has been moved to an appropriate selected position, retaining ring 213 is threaded forwardly toward stop 214 such that it forces leg 215 forwardly until it is fixedly retained in openings 308 and 218. As can be seen most clearly in FIG. 5, slot 308 and hole 218 are offset from the central longitudinal axis of the vibrator so as not to interfere with mandrel 202.

Mandrel 202 is formed with a threaded end 203 which is adapted to be received by threaded extension 43 of hollow shaft 42. The other end of mandrel 202 extends from the forward end of extension 201 and is also formed with a threaded end 204. A vertical bore 206 is formed in mandrel 202 and is adapted to receive an endodontic file 207. Typically, file 207 is formed with an enlarged head 208 to prevent it from slipping downwardly through bore 206. A threaded nut 205 is provided on the threaded end 204 of mandrel 202 to firmly secure file 207 within bore 206. A collar 209 is optionally provided between file 207 and the end of extension 201 in order to lessen the possibility of shearing file 207 when nut 205 is tightened.

Figures 6, 7, 8:
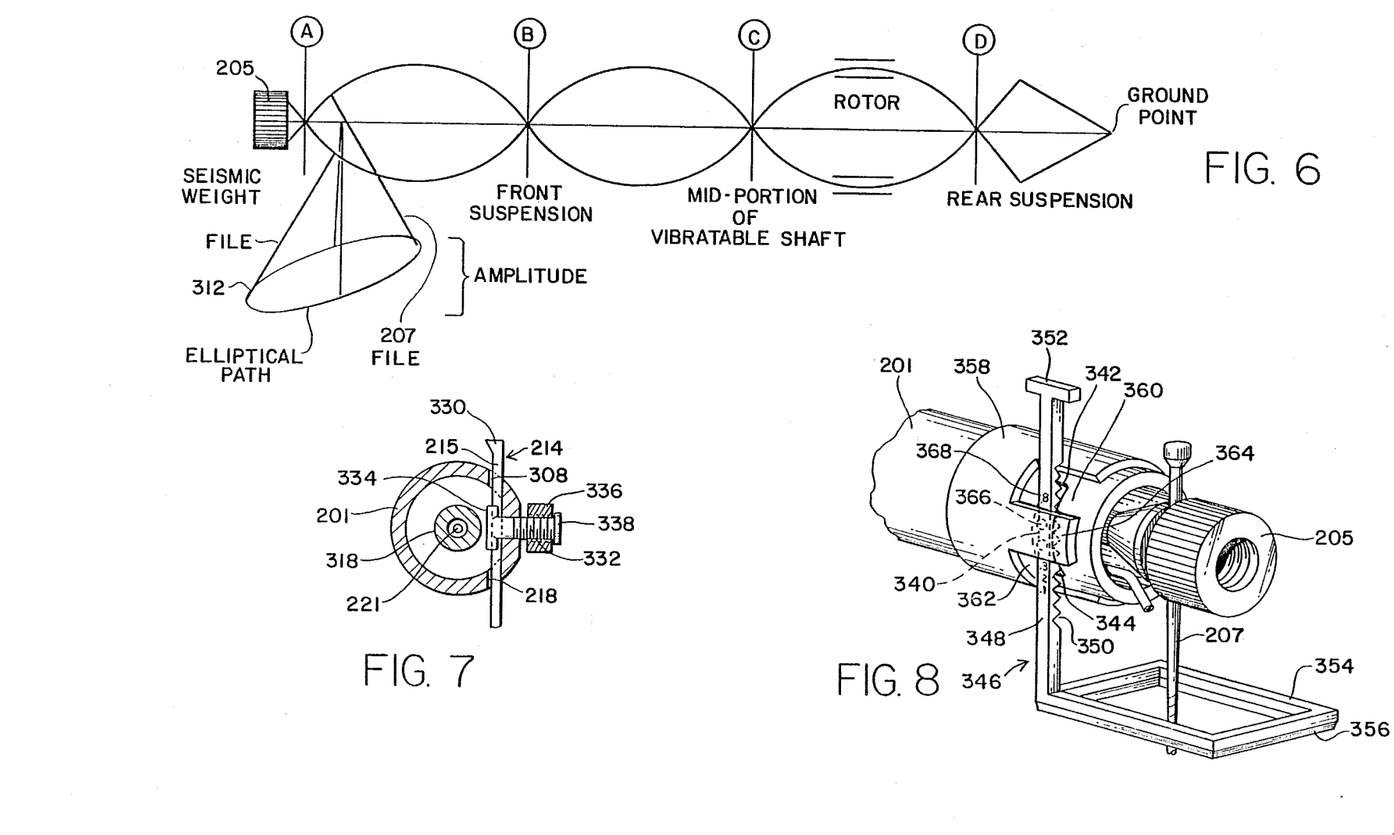
FIG. 6 is a schematic diagram of the vibrational characteristics of a device according to the present invention, particularly illustrating the simultaneous vertical and horizontal components of vibratory motion of the endodontic file.
FIG. 7 is a cross-sectional view of another embodiment of the stop means holding and adjusting mechanism of the present invention.
FIG. 8 is a perspective view of another embodiment of the stop means holding and adjusting mechanism of the present invention.

In a preferred embodiment of the invention, as illustrated in the schematic drawing of FIG. 6, threaded nut 205 is selected to have a optimal weight, depending on the size of the vibrator 10 and mandrel 202. Nut 205 is preferrably disposed to define a node (A) of the vibrational system formed by vibrator 10, mandrel 202 and file 207 depending upon the nut's weight, and, therefore acts as a seismic mass. The bore 206, and therefore file 207, are disposed between nodes of the vibrational system, causing a working end 132 of file 207 to move in an eliptical or circular path in which the elipse or circle is disposed at an angle to the longitudinal axis of the vibrator, giving working end 312 an up-and-down motion (proportional to the amplitude of the vibration at that off-tuned point of attachment) simultaneous with the circular or eliptical motion. Both the circular or eliptical motion and the up-and-down motion have been individually found to be very efficient to enlarge root canals and the like in teeth. The simultaneous combination of these horizontal and vertical motion components, as caused by the preferred tuning and structure of the device of the present invention, gives rise to an optimal mechanical advantage for endodontic procedures.

As can be seen from the structure previously described (See FIGS. 2 and 4), the stop member 214 is isolated from the vibrational transfer from hollow shaft 42 since it is suspended from housing 12, and not mandrel 202 which is directly connected to the vibrating member. Since hollow shaft 42 is resiliently supported within housing 12 by supports 30 and 32, minimal vibrational transfer occurs between hollow shaft 42 and housing 12. The use of optional cushioned portion 310 further prevents the transfer of vibration between a tooth being operated on and stop member 214. Stop member 214 is thereby effectively isolated from the vibrational transfer, making accurate depth placement of the end of file 207 is possible. Furthermore, because minimal vibrations are transferred to stop member 214, the failure life of stop member 214 is accordingly extended.

Stop member 214 is advantageously formed from a square wire or a rectangular wire such that it can be automatically oriented with respect to the file 207 in the proper position by placement in a rectangular or square-shaped opening such as 218 and 308. It then is only necessary that the stop member 214 be moved vertically up or down to position it with respect to the end of file 207 for proper placement. Stop surface 216 is conveniently placed such that it circumscribes at least a portion of file 207 but does not touch the file during any of the vibratory motion imparted thereto. In that configuration, stop surface 216 is positioned to contact the tooth surface during use without regard to the particular orientation of the vibratory device 10 when the file 207 is located within the tooth during use.

In many instances it is desirable to provide a fluid, often containing a medicament, to the working end of file 207. Such can be accomplished by utilizing the vibrator described in FIG. 2 and the work tool assemby, particularly as illustrated in FIG. 4. As shown in FIG. 4, the mandrel 202 is formed with a longitudinal bore 220 into which is inserted a tube 221. A distal end 314 of tube 221 conveniently extends a short distance out from an opening 316 in a distal end member 318 of mandrel 202, and fluid flow can be directed directly on to file 207 or on to a tooth being operated on. A proximal end 320 of tube 221 is in fluid communication with plenum 108 to receive and transport fluid from the vibratory device.

Various alternative embodiments for attaching the file 207 and stop member 214 to the mandrel 202 are illustrated in FIGS. 7-22. For example, an internal stop member holding embodiment is illustrated in FIG. 7, where a stop member 214 is shown disposed through openings 218 and 308. Stop member 214 has an enlarged portion 330 to prevent it from accidentally falling through the openings. A threaded member 332 slidingly extends through a side of extension 201, past the point through which the stop member passes, and is connected to a block 334. A reciprocally threaded member 336 is disposed on threaded member 332, which also has an enlarged end 338. By tightening the reciprocally threaded member 336, the threaded member 332 is urged towards the side wall of extension 201, thereby tightening block 334 against the upper leg 215 of stop member 214 and holding it in place. In another embodiment of the internal stop member holding concept (not shown) a conduit can be disposed between openings 218 and 308 to help guide the support leg between the openings. The conduit may be provided with means to displace it with respect to the line between the openings, thereby tending to hold the stop member in place.

Turning to FIG. 8, a side slot with stop holding means embodiment is shown having a vertical slot 340 disposed in the side wall of extension 201, and having an upper cross-sectional portion 342 of extension 201 and a lower cross-sectional portion 344. A stop member 346, having an upper leg 348, optionally with serrations 350 disposed into one side of it, and optionally with an enlarged portion 352 on its top, and also having a lower leg 354 with a cushioned portion 356 for encircling a file, is disposed in the slot. A stop member retaining means, such as a slidable sleeve 358 is disposed about extension 201 and has two recessed portions 360 and 362 with a central tab 364 between them. Tab 364 can also have urging means 366, such as a spring loaded ball bearing, disposed on the inside thereof. Upper leg 348 optionally has a series of markings 368 on its side opposite serrations 350, so that by placing stop member 346 inside slot 340 and aligning the marking 368 with a portion of the central tab 364 the depth of the stop member can be selectively set and held in place by the reciprocal action of the serrations 350 receiving the cross-sections 342 and 344, whereupon sleeve 358 is slid forward, where together with urging means 366, it holds the stop member in place. Additional retention members (such as a series of internally disposed bearings on the sleeve and a receiving groove disposed in the housing—not shown) may be associated with the sleeve in order to hold it in its closed position with respect to the stop member. Readjustment of the stop member is very easy using the invention according to this embodiment.

Figures 9, 10:
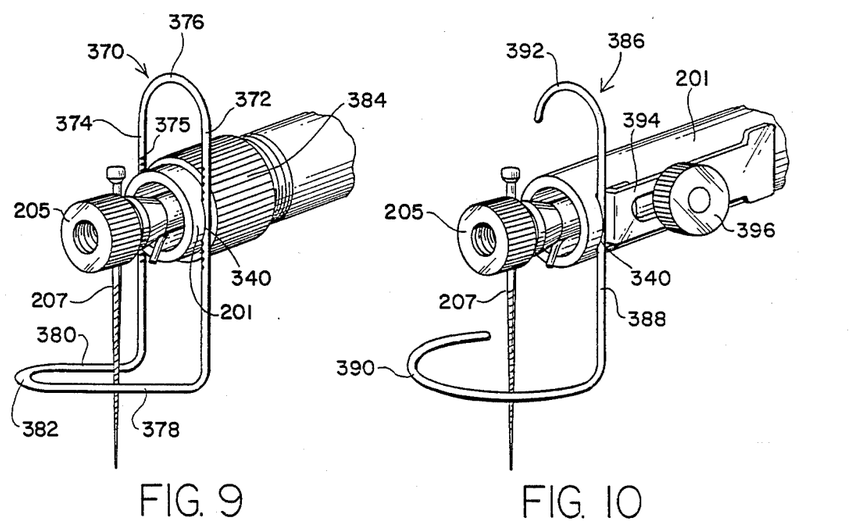
FIG. 9 is a perspective view of another embodiment of the stop means holding and adjusting mechanism of the present invention.
FIG. 10 is a perspective view of another embodiment of the stop means holding and adjusting mechanism of the present invention.

Turning to FIG. 9, the extension 201 is provided with a pair of slots 340 into which a spring clip type stop member 370 is disposed. Stop member 370 has a pair of upper legs 372 and 374 connected by a rounded top portion 376, and a pair of lower legs 378 and 380 also connected by a rounded portion 382. A threaded sleeve 384 is disposed around extension 201 such that by turning the sleeve, it will be urged against upper legs 372 and 374 thereby holding them in place. The rounded top portion 376 is particularly advantageous in that it is unlikely to pierce a rubber dam. The stop member 370 is attached by being yieldingly slid over the top of extension 201 into the slots 340. Alternatively, as shown in FIG. 9, the support legs 372 and 374 may be provided with internally disposed serrations 375 which will be urged against the cross-section of housing 201 formed by the upper and lower ends of slots 340, thereby holding stop member 370 in place without additional retaining means such as sleeve 384.

In FIG. 10 an adjustable side pressure stop member retaining embodiment is illustrated, wherein a stop member 386, similar to stop member 370 is shown as having a single upper leg 388 and a lower leg 390 looping aroung a file 207. Upper leg 388 is received in a slot 340, and has a curved upper portion 392 to avoid piercing a rubber dam. A side-mounted holding member 394 is movable against upper leg 388 of stop member 386 by a tightenable member 396 which is received in a side of extension 201.

Figure 11:
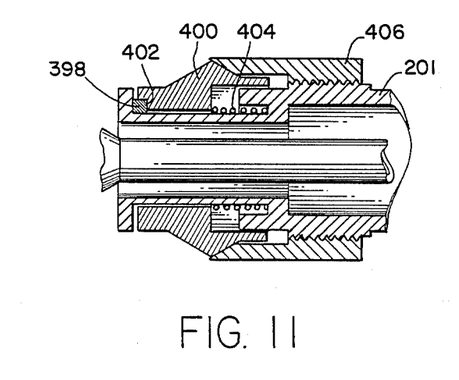
FIG. 11 is a cross-sectional view of another embodiment of the stop means holding and adjusting mechanism of the present invention.

Referring to FIG. 11, a stop member 398 is shown held in place in a slot or a hole by a spring-loaded member 400. Member 400 has a shoulder 402 designed to surround the stop member 398. The forward urging of a spring 404 maintains the member 400 against the stop 398 when a sleeve 406 is moved back, thereby permitting height adjustment of the stop member 398 and at the same time preventing it from dislodging from the instrument. Member 400 must be moved back, against the force of the spring 404 in order to remove the stop member completely. The stop member can be locked in place by moving the sleeve 406 forward.

Figure 12:
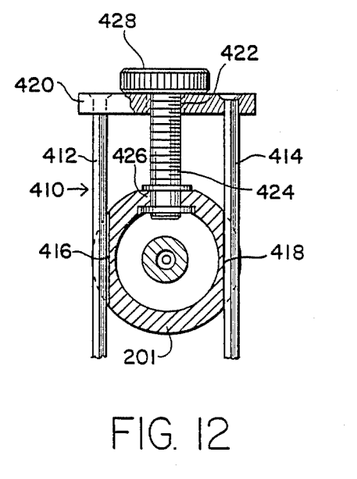
FIG. 12 is a cross-sectional view of another embodiment of the stop means holding and adjusting mechanism of the present invention.

Turning to FIG. 12, a screw thread mounted adjustable stop member is shown, wherein a stop member 410 having a pair of upper legs 412 and 414 disposed through a pair of receiving openings or slots 416 and 418 in extension 201 has an upper cross member 420 with a threaded opening 422 therethrough. A reciprocally threaded elongated member 424, such as a bolt, is turnably held in a top portion 426 of extension 201 and received in the opening 422. A knob 428 is fixedly attached to the top of elongated member 424 for turning it and thereby raising or lowering stop member 410.

Figure 13:
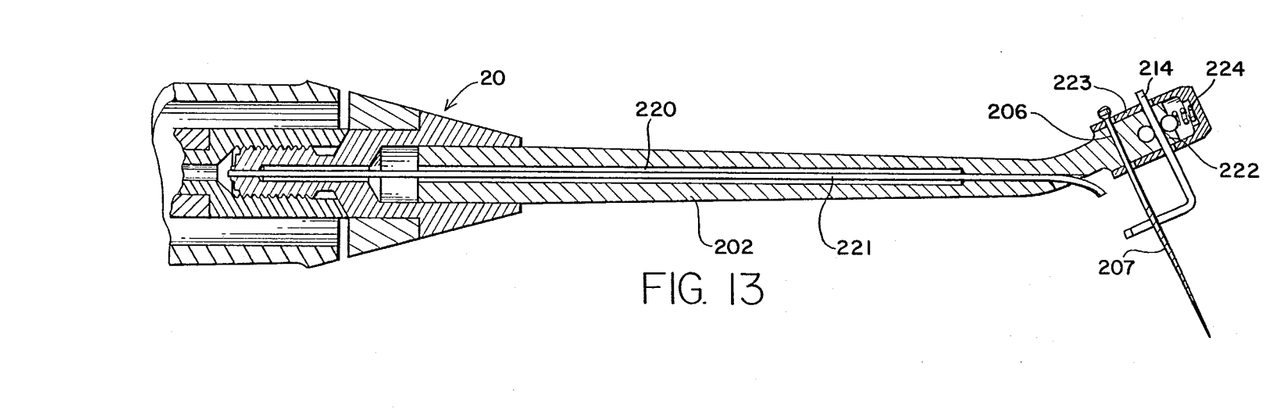
FIG. 13 is an enlarged side view, partially in section, of another embodiment of a work tool assembly of the present invention, shown incorporating fluid transport means.

As illustrated in the alternate embodiment of FIG. 13, the head portion of mandrel 202 can be formed with vertical bores 206 and 222 which are adapted to receive file 207 and stop member 214, respectively. An end cap 223 having holes to accommodate the ends of file 207 and stop 214 is placed about the head of mandrel 202 and can be conveniently spring loaded with spring 224 to retain file 207 and stop member 214 in selected positions. It will be apparent that a longitudinal bore such as bore 220 and a conduit such as tube 221 can be suitably placed within mandrel 202 which is illustrated in FIG. 4. Such an irrigation feature is considered to be within the presently preferred embodiments.

Figure 14:
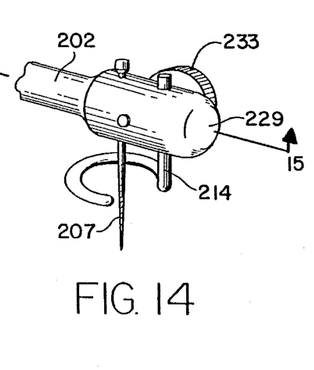
FIG. 14 is a perspective view of another embodiment of the file and stop means holding and adjusting mechanism of the present invention.
Figure 15:
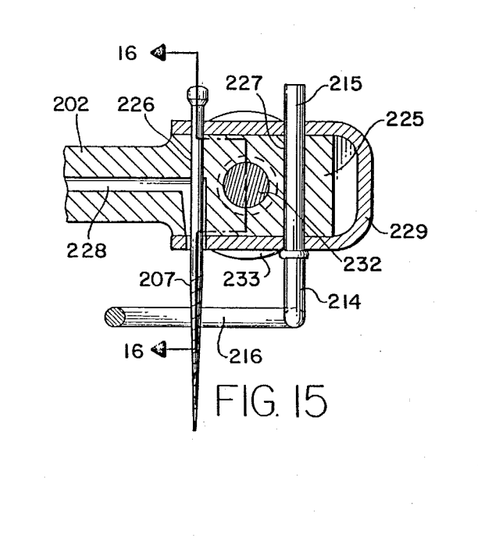
FIG. 15 is a cross-sectional view of the embodiment of the file and stop means holding and adjusting mechanism of the present invention, taken along line 15—15 in FIG. 14.
Figure 16:
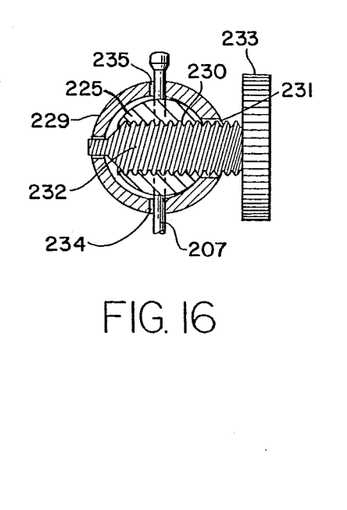
FIG. 16 is a cross-sectional view of the embodiment of the file and stop means holding and adjusting mechanism of the present invention, taken along line 16—16 in FIG. 15.

As shown in FIGS 14, 15 and 16, the mandrel 202 can be formed with a substantially cylindrical mandrel head 225 having a vertical bore 226 and a vertical bore 227 adapted to receive file 207 and stop member 214, respectively. Mandrel 202 can be provided with a longitudinal bore 228 which intersects bore 226 and provides a flow channel for transporting fluid to the end of file 207. File 207 and stop member 214 are fixedly retained in head 225 by means of a retaining tube 229 which is formed with top and bottom holes, designated as 235 and 234, respectively, to receive the upper ends of file 207 and stop member 214. The inner diameter of retaining tube 229 is made somewhat larger than the outer diameter of head 225 of mandrel 202. Mandrel 202 is provided with a transverse bore 230 which is internally threaded and adapted to receive a screw 232 which enters retaining tube 229 through a horizontal hole 231 formed in one side thereof. Conveniently a thumb wheel 233 is connected to screw 232 to assist the operator in its inward and outward movement. As can be seen most clearly in FIG. 16, tightening of screw 232 moves retaining tube 229 to a position which forces file 207 and stop member 214 against the walls of their respective receiving bores in head 225 of mandrel 202. That force effectively maintains file 207 and stop member 214 in fixed positions during use.

Figures 17, 18:
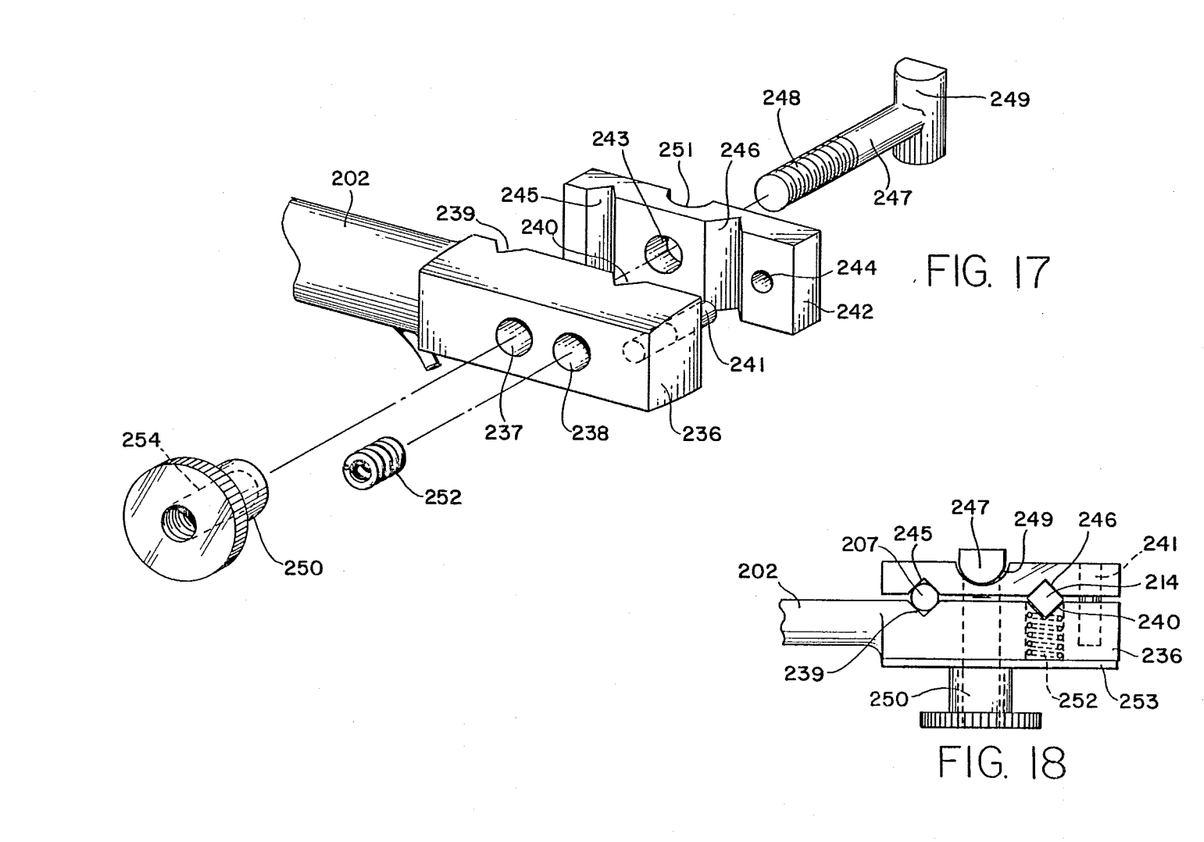
FIG. 17 is an exploded view of another embodiment of the stop member and endodontic tool holding and adjusting means of the present invention.
FIG. 18 is a top view of the embodiment of FIG. 17, shown assembled together and partly in section.

In still another embodiment, as can be seen in FIGS. 17 and 18, mandrel 202 is formed with a substantially rectangular head 236 having transverse bores 237 and 238 and vertical grooves 239 and 240. Vertical grooves 239 and 240 are adapted to receive file 207 and stop member 214, respectively, as can be seen most clearly in FIG. 18. A locating pin 241 is conveniently fixed to head 236. A retaining plate 242 is provided opposite the grooved face of head 236, and retaining plate 242 is formed with a bore 243 and a hole 244. Bore 243 is adapted to receive a bolt 247 and is aligned with bore 237 in head 236. Bore 244 is adapted to receive locating pin 241 and the interaction of pin 241 with retaining plate 242 serves to prevent twisting of retaining plate 242 when the head 236 and retaining plate 242 are fastened together. Vertical grooves 245 and 246 are provided in the mating face of retaining plate 242 and are adapted to receive file 207 and stop member 214, respectively, as can again be seen most clearly in FIG. 18. A substantially cylindrical groove extending vertically along the other face of retaining plate 242 is provided and groove 251 is dimensioned to mate with curved surface 249 formed on bolt 247. Retaining plate 242 and head 236 are secured by the engagement of bolt 247 on its threaded end 248 and a threaded nut 250. Bolt 247 extends through bores 243 and 237 and is received in threaded bore 254 in nut 250. A spring 252 is provided in bore 238 to load stop member 214 and minimize the vibration transmitted to stop member 214 during use of the instrument. A washer 253, as seen most clearly in FIG. 18, can be interposed between nut 250 and the end of spring 252 to effectively retain spring 252 within bore 238.

Figure 19:
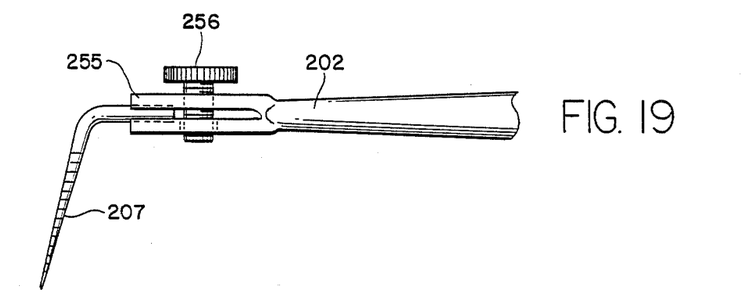
FIG. 19 is a side elevatinal view of another embodiment of the endodontic tool holding means of the present invention.
Figure 20:
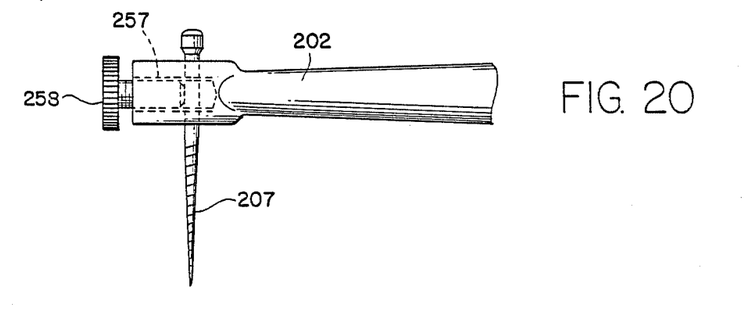
FIG. 20 is a side elevational view, partly in section, of another embodiment of the endodontic tool holding means of the present invention.
Figure 21:
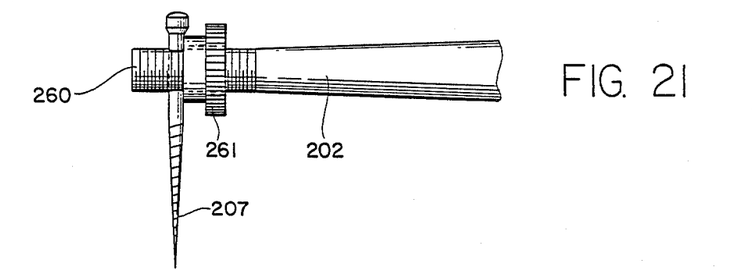
FIG. 21 is a side elevatinal view, partly in section, of another embodiment of the endodontic tool holding means of the present invention.
Figure 22:
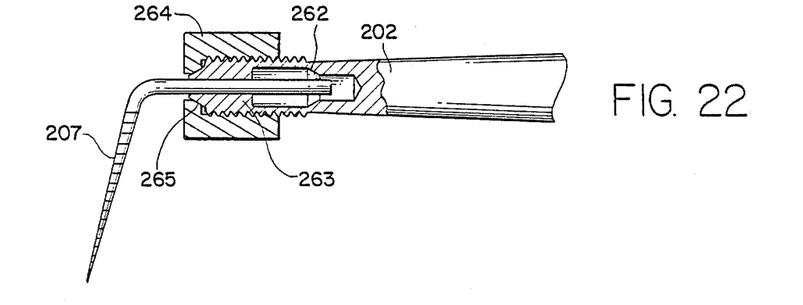
FIG. 22 is a side elevational view of another embodiment of the endodontic tool holding means of the present invention.

As shown in FIG. 19, mandrel 202 is provided with a split end 255 having a threaded bore and a screw 256 inserted therein. File 207 is inserted within the legs formed in split end 255 and can be retained therein by the pressure of screw 256. In FIG. 20, mandrel 202 is provided with an internally threaded bore 257 in which is inserted a threaded screw 258 which bears against file 207 to retain it thereon. In FIG. 21, the mandrel 202 is formed with a threaded end 260 having a bore there through to receive file 207. A captured, threaded nut 261 is positioned between file 207 and the vibratory portion of the device and can be tightened to press file 207 toward the forward end of end 260 to retain it thereon. In FIG. 22, mandrel 202 is provided with a tapered bore 262 into which is inserted a collet 263 having split, tapered ends. A nut 264 having an internal tapered surface 265 is threadely received on the threaded end of mandrel 202. File 207 is received in collet 263 and when nut 264 is tightened, the tapered ends of collet 263 interact with the corresponding tapered surfaces of nut 264 and bore 262 to firmly grip file 207 and hold it in place.

While this invention has been described with reference to specific embodiments thereof, it should be understood by those skilled in this art that various changes may be made and an equivalents may be substituted without departing from the true spirit and scope of the invention. For example, the stop member of the invention can be used with mechanically driven devices which oscillate the file in a rotary or linear fashion. It can also be used with other dental instruments such as drills and manual files, or with other surgical instruments such as bone cutting and drilling instruments used in orthopedic, neurological and similar procedures. It is, however, particularly suited for use within the limited space of the mouth. In addition, the various novel elements, as described herein can be used individually or collectively, as desired. All such modifications are intended to be within the scope of the claims appended hereto.

What is claimed is:

1. A vibratory device comprising:
   a housing;

vibratory drive means within said housing;
means supporting said vibratory drive means within said housing, said support means substantially preventing the transfer of vibration between said vibratory drive means and said housing;
a work tool operatively connected to said vibratory drive means;
an adjustable stop means operatively connected to said housing for limiting travel of said work tool between selected positions during use of said vibratory device; and
means for substantially isolating said stop means from vibration created by said vibratory drive means;
wherein said adjustable stop means comprises a support leg and a stop arm extending from said support leg, at least a portion of said support leg being adjustably received within a slot disposed in a side wall of said housing.

2. The vibratory device of claim 1 including slidable sleeve means disposed around said housing for movement into frictional engagement with said stop means.

3. The vibratory device of claim 2 wherein said slidable sleeve means has a pair of recessed portions and a tab between them, said recessed portions corresponding to said support leg at the points where it emerges from said slot and said tab corresponding to said support leg portion that is received in said slot, whereby said tab retains said stop means within said slot to hold said support leg at a fixed selected distance from a free end of said work tool.

4. The vibratory device of claim 3 wherein said tab comprises internally disposed urging means to force said support leg into said slot.

5. The vibratory device of claim 3 wherein said tab comprises a member directed towards and receivable within one of a plurality of reciprocal areas in said support leg for holding it at a desired position.

6. The vibratory device of claim 3 wherein said support leg outside has a depth scale associated therewith for illustrating the difference in length between said stop arm and an end of end said work tool.

7. The vibratory device of claim 2 wherein said slidable sleeve means comprises internally directed, spring loaded bearings for receipt within a groove disposed in said housing for maintaining said slidable sleeve means in a closed relationship with said stop means.

8. The vibratory device of claim 1 wherein said support leg comprises a series of serrations, or receiving a cross-sections of said housing formed at both ends of said slot, whereby said serrations hold said stop means against said housing at any desired position with respect to said work tool.

9. The vibratory device of claim 1 including stop means retaining means mounted on a side of said housing for being adjustably urged against said stop means to hold it in said slot.

10. The vibratory device of claim 1 which is a vibratory endodontic device, wherein the work tool is an endodontic work tool.

11. A vibratory device comprising:
a housing;
vibratory drive means within said housing;
means supporting said vibratory drive means within said housing, said support means substantially preventing the transfer of vibration between said vibratory drive means and said housing;
a work tool operatively connected to said vibratory drive means;
an adjustable stop means operatively connected to said housing for limiting travel of said work tool between selected positions during use of said vibratory device; and
means for substantially isolating said stop means from vibration created by said vibratory drive means;
wherein said stop means is a spring clip type stop means; and
wherein said housing has a pair of slots disposed therethrough for receiving said spring clip type stop means.

12. The vibratory device of claim 11 wherein said spring clip type stop means comprises a pair of support legs connected at their top by a blunt connection portion, and a pair of stop arms connected at a first end respectively to said pair of support legs and connected together at a second end by a connection portion, whereby said spring clip type stop means can be bent around said housing to be received within said slots, returning to its original shape once received within said slots.

13. The vibratory device of claim 12 wherein said support legs include an internally directed serrated portion for engagement, due to the compressive restorative force urging said support legs towards each other after being received within said slots, with upper and lower cross-sectional portions of said housing as defined by the upper and lower ends of said slots, whereby said serrations retain said stop means within said slots at any selected position for vertical placement of said top arms with respect to said working tool.

14. The vibratory device of claim 12 comprising a slidable locking means disposed on said housing for engagement with said stop means to hold it within said slots at any selected position for vertical placement of said stop arms with respect to said working tool.

15. The vibratory device of claim 14 wherein said slidable locking means is spring loaded towards said stop means.

16. The vibratory device of claim 11 which is a vibratory endodontic device, wherein the work tool is an endodontic work tool.

17. A vibratory device comprising:
a housing;
vibratory drive means within said housing;
means supporting said vibratory drive means within said housing, said support means substantially preventing the transmission of vibration between said vibratory drive means and said housing;
a work tool; and
an attachment assembly for operatively connecting said work tool with said vibratory drive means to be driven thereby;
wherein said attachment assembly comprises:
an attachment means having:
a first end having a threaded portion for connection to a reciprocally threaded end portion of said vibratory drive means,
a second end having a threaded portion,
a perpendicular passage through said attachment means near said second end for receiving said work tool, and
a work tool engaging member having a reciprocally threaded extension for connection with said threaded portion of said second end and a surrounding grasping portion having an annular shoulder extending toward said thread for impingement against said work tool to retain it in place with said passage upon said engaging member being screwed onto said threaded portion.

18. The vibratory device of claim 17 wherein said vibratory drive means generates an oscillatory motion perpendicular to its longitudinal axis and wherein said oscillatory motion is translated to said work tool as simultaneous perpendicular and parallel vibrations relative to the longitudinal axis.

19. The vibratory device of claim 17 wherein said work tool engaging member is a seismic mass defining the position of a node of the vibration of said device.

20. The vibratory device of claim 19 wherein said passage is disposed at a point between nodes of the vibration of said device.

21. The vibratory device of claim 19 wherein said passage is disposed at a node of the vibration of said device.

22. The vibratory device of claim 17 wherein said work tool has an enlarged upper portion having a size greater than the diameter of said passage, to prevent said work tool from slipping through said passage.

23. The vibratory device of claim 17 including fluid transport means disposed in a central passageway through said vibratory drive means and said attachment member to deliver fluid to the area of the work tool.

24. The vibratory device of claim 17, which further comprises:
   a stop means operatively connected to said housing for limiting travel of said work tool between selected positions during use of said vibratory device; and
   means for substantially isolating said stop means from vibration created by said vibratory drive means.

25. The vibratory device of claim 17 which is a vibratory endodontic device, wherein the work tool is an endodontic work tool.

* * * * *